United States Patent
Trebbi et al.

(10) Patent No.: US 11,174,055 B2
(45) Date of Patent: Nov. 16, 2021

(54) CONVEYOR ASSEMBLY FOR PACKAGES OF CONTAINERS FOR PHARMACEUTICAL USE

(71) Applicant: I.M.A. INDUSTRIA MACCHINE AUTOMATICHE S.P.A., Ozzano dell'Emilia (IT)

(72) Inventors: Claudio Trebbi, Medicina (IT); Gabriele Gabusi, Castenaso (IT)

(73) Assignee: I.M.A. INDUSTRIA MACCHINE AUTOMATICHE S.P.A., Ozzano dell'Emilia (IT)

( * ) Notice: Subject to any disclaimer, the term of this patent is extended or adjusted under 35 U.S.C. 154(b) by 112 days.

(21) Appl. No.: 16/321,441

(22) PCT Filed: Jul. 26, 2017

(86) PCT No.: PCT/EP2017/068855
§ 371 (c)(1),
(2) Date: Jan. 28, 2019

(87) PCT Pub. No.: WO2018/019871
PCT Pub. Date: Feb. 1, 2018

(65) Prior Publication Data
US 2019/0177019 A1     Jun. 13, 2019

(30) Foreign Application Priority Data
Jul. 27, 2016 (IT) .......................... 102016000078604

(51) Int. Cl.
*B65B 43/50* (2006.01)
*B65G 47/86* (2006.01)
(Continued)

(52) U.S. Cl.
CPC .............. *B65B 43/50* (2013.01); *A61L 2/16* (2013.01); *B65B 55/10* (2013.01); *B65G 47/842* (2013.01); *B65G 2201/0235* (2013.01)

(58) Field of Classification Search
CPC ......... B65B 39/00; B65B 43/42; B65B 43/46; B65B 43/50; B65B 43/54; B65B 55/10; B65G 47/842
(Continued)

(56) References Cited

U.S. PATENT DOCUMENTS 2,967,081 A    1/1961   Kleinpenning
5,746,258 A *  5/1998   Huck ...................... B65B 39/00
                                                         141/264

(Continued)

FOREIGN PATENT DOCUMENTS

| DE | 102011080289 A1 | 2/2013 |
| WO | WO-2013017315 A2 | 2/2013 |
| WO | WO-2016000718 A1 * | 1/2016 ............. B65B 61/12 |

OTHER PUBLICATIONS

International Search Report and Written Opinion for PCT/EP2017/068855, dated Oct. 17, 2017.

*Primary Examiner* — Chelsea E Stinson
(74) *Attorney, Agent, or Firm* — Marshall, Gerstein & Borun LLP

(57) ABSTRACT

A conveyor assembly for packages of containers for pharmaceutical use which include an outer bag. The assembly includes a handling line for gripping elements and a dispensing apparatus for a laminar flow of gas positioned above the top of the line and directed towards the line itself. Each gripping element includes at least one clamping jaw for at least one flap of said bag to hang it so that each of its outer surfaces is invested by the laminar flow of gas during its handling.

9 Claims, 2 Drawing Sheets

(51) Int. Cl.
*A61L 2/16* (2006.01)
*B65B 55/10* (2006.01)
(58) Field of Classification Search
USPC .......................................................... 53/510
See application file for complete search history.

(56) References Cited

U.S. PATENT DOCUMENTS

| | | | | |
|---|---|---|---|---|
| 6,164,044 | A | * 12/2000 | Porfano | ................. B65B 55/10 |
| | | | | 422/28 |
| 2006/0075721 | A1 | 4/2006 | Monti | |
| 2010/0005760 | A1* | 1/2010 | Matheyka | ............... B65B 55/08 |
| | | | | 53/426 |
| 2016/0122057 | A1* | 5/2016 | Takahashi | ............ B65B 43/465 |
| | | | | 53/284.7 |

* cited by examiner

CONVEYOR ASSEMBLY FOR PACKAGES OF CONTAINERS FOR PHARMACEUTICAL USE

BACKGROUND OF THE INVENTION

This invention pertains to a conveyor assembly for packages of containers for pharmaceutical use.

Field of the Invention

The packages are specifically intended for the containment and the separation with respect to the outer environment of containers such as vials, bottles, syringes, ampoules and the like.

These containers are subjected to cleaning and sterilizing treatments to ensure that there is no residue inside them (not even dust particles or similar) and to remove any contaminants from their surfaces.

These are normally assembled on a nest, which is also subject to similar treatments for cleaning and sterilization.

The nest is, in turn, placed inside a sterile tub with a protective sheet on top which prevents the entry of dust or other particles into the containers (which are positioned with their upper mouth open).

A sealing film is firmly affixed to the upper edges of the tub (containing the protective sheet, nest and containers) to completely isolate the inside of the tub from the outside.

The tub is then arranged within a bag (generally made of a polymeric material) that forms a second protective barrier (since the outside of the tub and the sealing film must still be sterile).

In this way it is possible to transport the containers, so packaged, with the guarantee that they will not be subjected to involuntary contamination.

Once the containers arrive at the plant where they will be filled with a variety of specific substances, it is necessary to handle them: first to transport them to the station where the bag will be opened, then to the station where the sealing film will be removed, and finally to the station where each individual container will be filled.

These operations will be performed in environments presenting a specific particle contamination class (filling operations will be performed in the environment with the lowest risk of contamination).

In the early phases of transport a laminar gas flow is used to infuse the conveyor belt and the bags on it, in order to eliminate the conveyance of particles which may have landed on the outside of the bag surface (accumulated during transport or storage).

This laminar flow removes such particles.

Generally, the bottom of a bag lays on a conveyor belt preventing the flow to clean the bottom of the bag and therefore these particles are not removed from the bag.

It is therefore found that the measures currently adopted to minimize the amount of particles on a bag have no effect on at least one of the sides of the bag (the bottom sitting on the conveyor belt).

The presence of a bag surface that is potentially contaminated by a considerably higher amount of particles than the other surfaces implies an overall deficiency of the measures taken so far for the removal of accumulated particles.

Among other things, contact of the bag bottom with the conveyor belt surface could also lead to the adhesion of particles from the belt to the bottom of the bag, without the possibility of removing them by means of the laminar flow.

Moreover, there is no certainty that bags will stay in place during transport, as well as not get damaged (e.g. a bent edge or surface) due to external actions or their own weight.

It is known from US 2016/0122057 a packaging machine for filling bags where the bags are hung by grips on an annular handling line.

SUMMARY OF THE INVENTION

The main aim of this invention is to solve the problems outlined above, providing a conveyor assembly for packages of containers for pharmaceutical use wherein the laminar flow will reduce the accumulation of particles on its outer surface, involving the entire outer surface of packages itself.

Within the scope of this undertaking, one purpose of the invention is to provide a conveyor assembly for packages of containers for pharmaceutical use which minimizes the risk of adhesion of further particles to the outer surface of the packages.

Another purpose of the invention is to propose a conveyor assembly for packages of containers for pharmaceutical use in which the bag remains fixed in place during all transport operations.

Another purpose of the invention is to propose a conveyor assembly for packages of containers for pharmaceutical use in which the bag does not get damaged as a result of external actions or due to its own weight.

Another purpose of the invention is to propose a fully automated conveyor assembly for packages of containers for pharmaceutical use.

A final purpose of this invention is to provide a conveyor assembly for packages of containers for pharmaceutical use of cost-effective, relatively simple implementation and practical, safe application.

This undertaking and these purposes are achieved through a conveyor assembly for packages of containers for pharmaceutical use according to claim 1.

BRIEF DESCRIPTION OF THE DRAWINGS

Further features and advantages of the invention will become more apparent from the description of a preferred, but not exclusive, implementation of the conveyor assembly for packages of containers for pharmaceutical use according to the invention. This is illustrated by way of non-limiting example in the accompanying drawings, in which.

DETAILED DESCRIPTION

Figure 1:
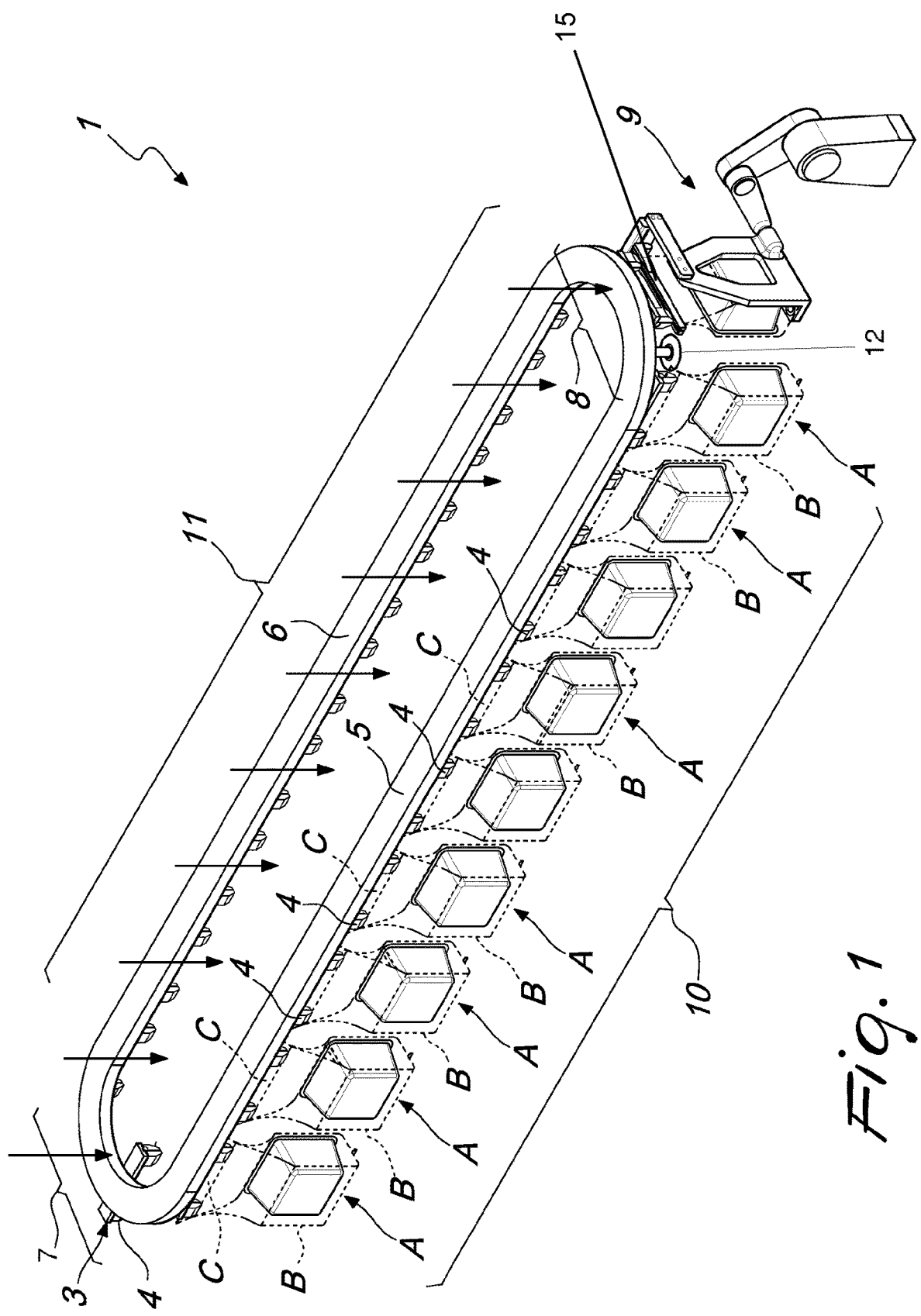
FIG. 1 represents, in schematic axonometric view, a conveyor assembly for packages of containers for pharmaceutical use according to the invention.
Figure 2:
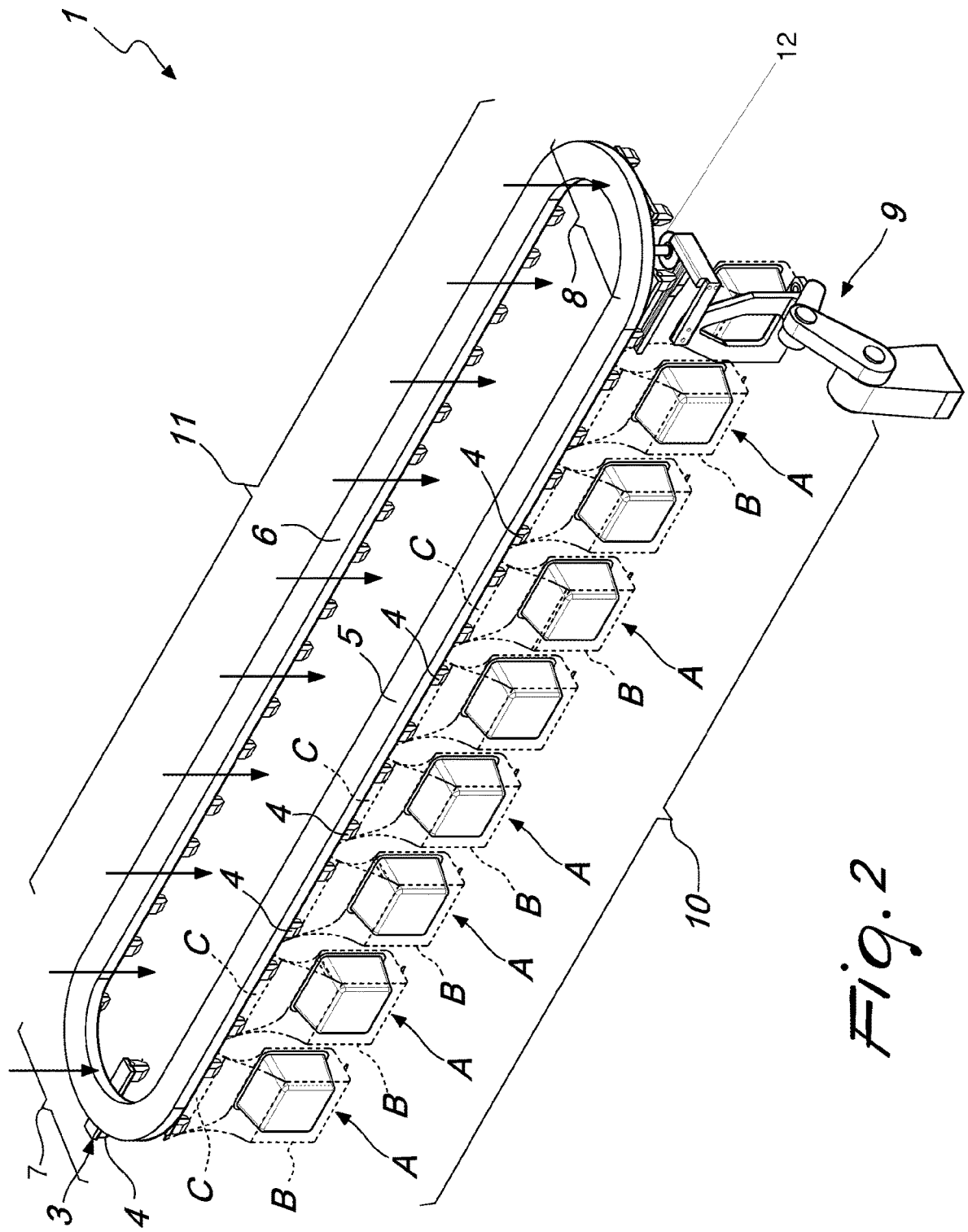
FIG. 2 represents, in schematic axonometric view, an alternative embodiment of a conveyor assembly for packages of containers for pharmaceutical use according to the invention.

With particular reference to these figures with reference sign 1 is globally indicated a conveyor assembly 1 for packages A of containers for pharmaceutical use according to the invention.

The packages A, according to the invention, includes an outer bag B, hermetically sealed and preferably made of a polymeric material.

The assembly 1 comprises a handling line 2 for gripping elements 3 and a dispensing apparatus for a laminar flow of gas positioned above the upper portion of line 2 and directed so as to invest it.

In the accompanying figures, the representative lines of the laminar flow of gas comprise a series of top-down arrows above the assembly 1 (this representation is only suggestive and does not impose any limitation on the type of gas circulation that will be possible to establish).

It is specified that each gripping element 3 comprises at least one clamping jaw 4 for at least one flap C of the bag B: due to the presence of the at least one jaw 4 it is possible to hang each bag B so that its outer surface is invested by the laminar flow of gas during its handling.

The laminar flow strikes the bags conveyed by the handling line 2.

When a bag B is hanging on at least one jaw 4 its position is constant and certain during handling operations, thus avoiding possible damage due, for example, to external actions and/or its own weight.

This arrangement is extremely advantageous because it ensures that no undesirable particle accumulation can occur on one of the outer surfaces of the bag B: in traditional handling assemblies, the bags B are placed on a conveyor belt. The belt surface is exposed to a laminar air flow, but it is not possible to prevent particle deposits on it.

In any case, when the bags are sitting on the belt surface, the side of the bag B in contact with the belt is not exposed to the flow and therefore any particle build-up (on the bottom of the bag B or on the belt) will not be affected by the flow and will not be removed.

The assembly 1 according to the invention, however, allows cleaning of all surfaces of each bag B by facilitating the removal of any particles accumulated on them and preventing the deposit of any other particles suspended in the air of the environment in which the assembly 1 is located.

Based on an implementation solution of undeniable practical and applicative potential, the handling line 2 is closed in a loop and driven by an automatic motor unit controlled by a control and management processor.

This configuration, identifying an active section 5 (along which the bags B are transported) and a passive section 6 (which instead only serves to bring the gripping elements back to the beginning of the active section 5) and using for transport only about half of the gripping elements 3 present, has the great advantage of moving continuously.

Instead of a continuous motion an alternating motion is also possible.

In order to accurately identify the characteristics of the bags B which can be processed with the assembly 1 according to the invention, it is specified that each bag B preferably has one tub, within which a nest, will be placed in turn, equipped with a plurality of seats for containers (syringes, vials, bottles, ampoules and similar).

Specifically, with particular reference to the pharmaceutical sector, the tub, nest and containers will be sterile, as they are previously subjected to cleaning and sterilizing phases in order to arrive in their packages inside the bag B without any contaminants.

With particular reference to the implementation solution represented by way of example and non-limiting in the attached figure, the handling line 2 comprises a first portion 7 aligned to a bag delivery station.

At that station, one bag at a time is transferred from a temporary storage area to a gripping area on the transfer line: in that gripping area the bag B presents its own upper flap C aligned and adjacent to the first portion 7 of the handling line 2 for delivery to the respective clamping jaws 4 of a corresponding gripping element 3.

In the context of this implementation, the handling line 2 can effectively include a second portion 8 aligned with a bag pickup station 9.

At the second portion 8, one bag B at a time will be conveniently taken for handling from a subsequent pickup station 9.

The pickup station 9 can comprise at least one cutting device 12 to conveniently remove the flap C from the bag B which is clamped between the jaws 4 of the respective gripping element 3.

The pickup station 9 includes securing elements 15 for a bag B and its contents.

The handling line 2 which is annular-shaped includes two intermediate portions 10 and 11 essentially linear and essentially parallel to each other.

These essentially linear portions 10 and 11 are interposed between the first portion 7, aligned to a bag transfer station, and the second portion 8, aligned with a bag pickup station 9.

According to a solution of undeniable operational potential, the dispensing apparatus for a laminar flow of gas comprises a ventilation compressor, a conveying duct connected downstream of the compressor, and a plurality of supply nozzles above the handling line 2.

In this way it is possible to generate a laminar gas flow from the top downwards that will surround all the bags B hanging from their respective gripping elements 3.

It is specified that the gas conveyed by the dispensing apparatus will preferably be air, previously filtered. Using other types of gas, such as inert gas, nitrogen and similar, is not excluded depending on the specific application requirements.

This invention solves the problems outlined above, proposing a conveyor assembly 1 for packages A of containers for pharmaceutical use in which the laminar flow of gas, intended to reduce the accumulation of particles on the relevant outer surfaces, invests the entire outside surface of the package itself. This benefit is particularly important as it ensures that no part of the packages A (in particular the outer bag B) may be subject to the accumulation or depositing of particles (which may contaminate the active ingredients and/or the substances that will be placed in the containers present inside the packages A).

According to the invention, the conveyor assembly 1 usefully minimizes the risk of adhesion of further particles to the outer surface of the packages A.

According to the invention, the conveyor assembly 1 is fully automated: it has the advantage of successfully avoiding problems and contaminations introduced by involuntary mistakes made by an operator.

The conveyor assembly 1 for packages A of containers for pharmaceutical use conveniently guarantees that the position of a bag B remains stable throughout all transport operations.

The conveyor assembly 1 for packages A of containers for pharmaceutical use efficiently guarantees that a bag B does not suffer damage as a result of external actions or due to its own weight.

According to the invention, the conveyor assembly 1 is effectively relatively simple to implement and cost-effective: these features make the assembly 1 a safe innovation to implement.

The invention thus conceived can receive numerous modifications and variants all within the scope of the inventive concept; moreover, all details may be replaced by other technically equivalent elements.

In the implementation examples illustrated, individual features and specific examples stated may in fact be interchanged with other different features from other implementations.

In practice, any materials of any size can be used, according to requirements and the state of the art.

The invention claimed is:

1. A conveyor assembly for packages of one or more containers for pharmaceutical use, said packages being contained in a plurality of bags, the conveyor assembly comprising:
   a handling line for moving gripping elements, each gripping element comprising at least one clamping jaw configured to clamp at least one flap of a respective one of the bags so that the respective bag hangs freely from the handling line; and
   a dispensing apparatus positioned above said handling line and configured to supply a laminar flow of a gas directed towards the handling line so that each respective bag is invested by said laminar flow during the conveyance of the respective bag hanging from the handling line,
   wherein the respective bag is in a sealed configuration when hanging from the handling line in order to preserve a sterility condition of the one or more containers inside the respective bag, such that the laminar flow invests only an external side of the respective bag, and wherein the respective bag remains in the sealed configuration while hanging from the handling line.

2. The conveyor assembly according to claim 1, wherein said handling line is closed in a loop and driven by an automatic motor unit which is controlled by a control and management processor.

3. The conveyor assembly according to claim 1, wherein the respective bag contains a sterile tub.

4. The conveyor assembly according to claim 1, wherein said handling line comprises a first portion aligned with a bag transfer station, where only a single bag at a time is transferred to a gripping area, in which said single bag is displaced in proximity to said first portion of said handling line in order to be clamped by the clamping jaws of one of the gripping elements.

5. The conveyor assembly according to claim 4, wherein said handling line comprises a second portion aligned with a bag pickup station, at which only the single bag at a time is taken from the handling line by said bag pickup station.

6. The conveyor assembly according to claim 1, including a bag pickup station having at least one cutting device for cutting the clamped flap of said bag thereby opening the bag, said bag pickup station configured to secure the bag during the cutting of the flap by the cutting device.

7. The conveyor assembly according to claim 5, wherein said handling line has an annular configuration and comprises two linear and parallel intermediate portions, with said linear and parallel intermediate portions being interposed between said first portion, aligned with the bag transfer station, and said second portion, aligned with the bag pickup station.

8. The conveyor assembly according to claim 1, wherein said dispensing apparatus for supplying a laminar flow of a gas comprises a plurality of supply nozzles positioned above said handling line.

9. The conveyor assembly according to claim 1, wherein said gas supplied by said dispensing apparatus is filtered air.

\* \* \* \* \*